US010087131B2

(12) United States Patent
Jackson et al.

(10) Patent No.: US 10,087,131 B2
(45) Date of Patent: Oct. 2, 2018

(54) PROCESS FOR THE PRODUCTION OF GLYCOLIC ACID

(71) Applicant: JOHNSON MATTHEY DAVY TECHNOLOGIES LIMITED, London (GB)

(72) Inventors: Simon Wayne Jackson, Durham (GB); Adam Armour Snaith, Durham (GB); Michael William Marshall Tuck, London (GB); David John Watson, Durham (GB)

(73) Assignee: Johnson Matthey Davy Technologies Limited, London, England (GB)

( * ) Notice: Subject to any disclaimer, the term of this patent is extended or adjusted under 35 U.S.C. 154(b) by 0 days.

(21) Appl. No.: 15/564,566

(22) PCT Filed: Mar. 23, 2016

(86) PCT No.: PCT/GB2016/050821
§ 371 (c)(1),
(2) Date: Oct. 5, 2017

(87) PCT Pub. No.: WO2016/162662
PCT Pub. Date: Oct. 13, 2016

(65) Prior Publication Data
US 2018/0086686 A1    Mar. 29, 2018

(30) Foreign Application Priority Data

Apr. 8, 2015    (GB) .................................. 1505981.9

(51) Int. Cl.
| C07C 51/10 | (2006.01) |
| C07C 51/12 | (2006.01) |
| B01J 31/02 | (2006.01) |
| B01J 21/08 | (2006.01) |

(52) U.S. Cl.
CPC .............. *C07C 51/12* (2013.01); *B01J 21/08* (2013.01); *B01J 31/0225* (2013.01); *B01J 31/0274* (2013.01)

(58) Field of Classification Search
CPC ......... C07C 51/12; B01J 21/08; B01J 31/274; B01J 31/225
See application file for complete search history.

(56) References Cited

U.S. PATENT DOCUMENTS

| 2,152,852 A | 4/1939 | Loder |
| 2,285,448 A | 6/1942 | Loder |
| 2,443,482 A | 6/1948 | Shattuck |
| 3,911,003 A | 10/1975 | Suzuki |
| 4,016,208 A | 4/1977 | Suzuki |
| 4,052,452 A | 10/1977 | Scardigno et al. |
| 4,087,470 A | 5/1978 | Suzuki |
| 4,136,112 A | 1/1979 | Bakshi |
| 4,140,866 A | 2/1979 | Nielsen |
| 4,188,494 A | 2/1980 | Suzuki |
| 4,431,486 A | 2/1984 | Balmat |
| 6,376,723 B2 | 4/2002 | Drent et al. |
| 2010/0290962 A1 | 11/2010 | Wilson et al. |
| 2013/0261333 A1 | 10/2013 | Barnicki et al. |

FOREIGN PATENT DOCUMENTS

| DE | 3133353 A1 | 3/1983 |
| EP | 0114657 A1 | 8/1984 |
| EP | 1360222 A1 | 11/2003 |
| EP | 1786850 A1 | 5/2007 |
| GB | 1499245 A | 1/1978 |
| JP | S56073042 | 6/1981 |
| JP | 2503178 | 8/1994 |
| KR | 1995009480 | 8/1994 |
| KR | 19950011114 B1 | 9/1995 |
| KR | 0124821 | 12/1997 |
| KR | 1019950013078 B1 | 11/1998 |
| KR | 0155273 | 12/1998 |
| WO | WO2002/055587 A1 | 7/2002 |
| WO | WO2006/013060 A1 | 2/2006 |
| WO | WO2006013080 A1 | 2/2006 |
| WO | WO2007090676 A1 | 8/2007 |
| WO | WO2009/140787 | * 11/2009 |
| WO | WO2009140787 A1 | 11/2009 |
| WO | WO2009140788 A1 | 11/2009 |
| WO | WO2009140850 A1 | 11/2009 |
| WO | WO2013148497 A1 | 10/2013 |

OTHER PUBLICATIONS

Gill et al., Journal of Catalysis, vol. 251(1), 2007, pp. 145-152.
GB1604956.1, Combined Search and Examination Report under Sections 17 and 18(3) dated Jan. 26, 2017.
PCT/GB2016/050821, International Search Report, dated Jan. 6, 2016.
PCT/GB2016/050821, Written Opinion dated Jan. 6, 2016.
He et al., Condensation of Formaldehyde and Methyl Formate to Methyl Glycolate and Methyl Methoxy Acetate Using Heteropolyacids and Their Salts, Catalysis Today, vol. 51, Issue 1, Jun. 1999, pp. 127-134.

* cited by examiner

*Primary Examiner* — Yevgeny Valenrod
*Assistant Examiner* — Blaine G Doletski
(74) *Attorney, Agent, or Firm* — Baker & Hostetler LLP

(57) ABSTRACT

A process for the production of glycolic acid or derivatives thereof from formaldehyde comprising reacting formaldehyde with carbon monoxide and water in the presence of a silica catalyst, wherein from about 200 to about 5000 ppm of an alkyl silyl sulfonic acid is supplied to the reaction.

17 Claims, 1 Drawing Sheet

PROCESS FOR THE PRODUCTION OF GLYCOLIC ACID

CROSS-REFERENCE TO RELATED APPLICATIONS

Figure 1:
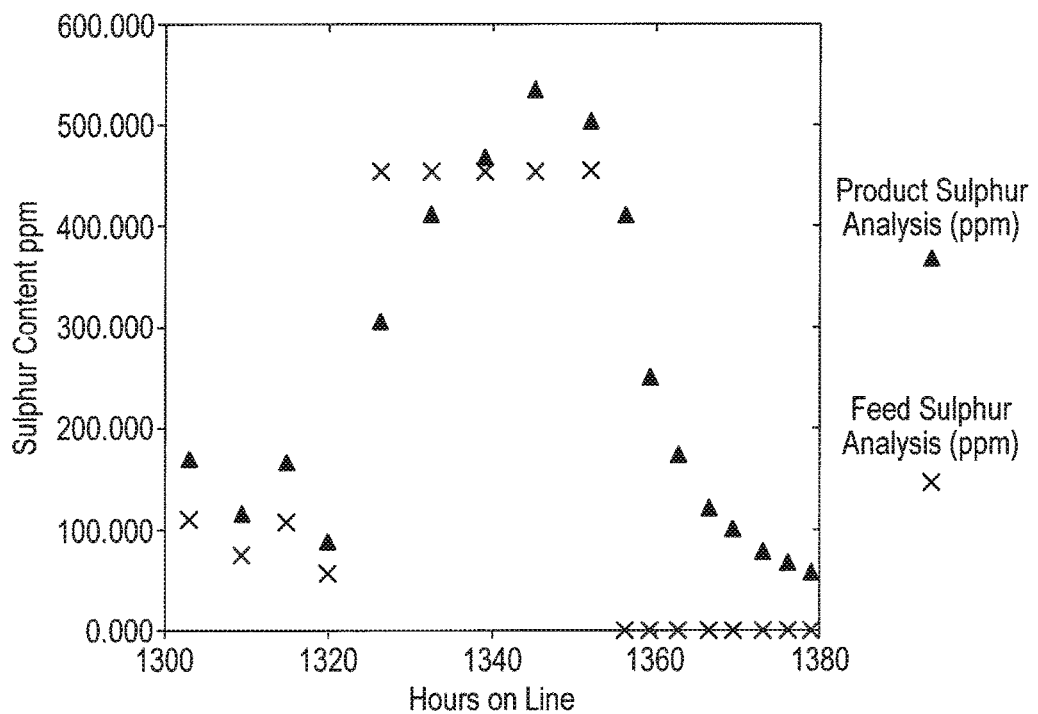

This application is the National Stage of International Patent Application No. PCT/GB2016/050821 filed Mar. 23, 2016, which claims priority from Great Britain Patent Application No. 1505981.9 filed Apr. 8, 2015, the disclosures of each of which are incorporated herein by reference in their entirety.

The present invention relates to a process for the production of an acid, in particular glycolic acid.

The reaction to form glycolic acid by the carbonylation of formaldehyde with carbon monoxide and water using strong acid catalysts is well known. The basic process was first disclosed by DuPont in U.S. Pat. No. 2,152,852. The process was for the preparation of glycolic acid in the liquid phase by reacting formaldehyde, water and carbon monoxide in the presence of a homogeneous acidic catalyst at temperatures between 50° C. and 350° C. and at a pressure between 5 and 1500 atma. Sulfuric acid, hydrochloric acid, phosphoric acid, boron fluoride, formic acid and glycolic acid are identified as being suitable catalysts.

DuPont went on to obtain further patents in this field, including U.S. Pat. No. 2,285,448, which related to the hydrogenation of glycolic acid to ethylene glycol, and U.S. Pat. No. 2,443,482 which related to a continuous process for formaldehyde carbonylation.

The process for producing ethylene glycol was commercialised and operated by DuPont until the late 1960's when this route to ethylene glycol became uncompetitive. The plant was then operated for the production of glycolic acid in which sulfuric acid was used as catalyst at a temperature of 200° C. and at a pressure of from 400 to 700 bar.

The processes described in these initial cases suffered from numerous problems. These problems included those attributable to the need to operate at very high pressure. In addition, the selectivity was poor. It was also necessary to contend with the highly corrosive reaction mixture and the difficulty of removing the homogeneous acid catalyst such as sulfuric acid from the reaction product.

Various proposals have been made to address some or all of these problems. For example, U.S. Pat. No. 3,859,349 attempts to address the problems associated with separating the sulfuric acid catalyst and suggests using ion exchange resins as an alternative to neutralisation with calcium carbonate, which had been the previous approach. However, the sulfonic acid based ion exchange resins have limited thermal stability in aqueous environments leading to the loss of acid groups.

Another proposal was that described in U.S. Pat. No. 4,431,486 in which azeotropic distillation of the crude glycolic acid product was proposed as a means of reducing the water content in the recycle to the carbonylation reactors thereby minimising byproduct formation and increasing the yield from the feed formaldehyde.

Another approach has been to look at alternative catalyst systems as a means of reducing the reactor operating pressure. Hydrogen fluoride has been suggested as being a suitable catalyst in U.S. Pat. No. 3,911,003, U.S. Pat. No. 4,016,208, U.S. Pat. No. 4,087,470, U.S. Pat. No. 4,136,112 and U.S. Pat. No. 4,188,494. Processes which use hydrogen fluoride in place of sulfuric acid as catalyst are suggested to allow operating pressures of 1 to 275 bar.

A further alternative process is disclosed in U.S. Pat. No. 4,052,452 in which CO) or Ag salts in concentrated sulfuric acid are suggested as a means of increasing the carbon monoxide solubility and it is suggested that this enables the operating pressure to be reduced to between 0.1 and 30 atma. Whilst this may address the operating pressure issues, such systems are extremely sensitive to poisoning by water and separation and recycle of the metallic catalyst is difficult.

In U.S. Pat. No. 6,376,723 it is proposed that the reaction should be conducted with an acid catalyst having a pKa value of less than −1 in the presence of a sulfone as a means of moderating the reaction conditions. There is also a suggestion that heterogeneous catalysts could be used.

U.S. Pat. No. 4,140,866 looks at the problems associated with removing the sulfuric acid catalyst from glycolic acid produced by formaldehyde carbonylation. The proposed solution is to first treat the reaction mixture with an alkali metal hydroxide to form the dissolved sulfate salt and this is then precipitated on esterification of the glycolic acid with ethylene glycol and removal of water.

A widely adopted strategy for overcoming the problems associated with separating homogeneous catalysts from reaction mixtures is to replace the homogeneous catalysts with heterogeneous catalysts that can easily be mechanically separated. Several solid acid materials have been suggested as suitable catalysts for formaldehyde carbonylation. These include sulfonic acid ion exchange resins, aluminosilicate zeolites, polyoxometalate salts and alkyl sulfonic acid polysiloxanes.

The use of solid insoluble particulate acidic catalysts having a hydrogen ion exchange capacity in excess of 0.1 milliequivalents per gram was first described in GB1499245. Sulfonic acid based ion-exchange resins, acid clays and zeolites are listed as suitable catalysts. Strongly acidic cation exchange resins in a reaction solvent such as acetic acid are suggested in JP56073042A2 and the use of FZ-1 and ZSM type zeolites in EP0114657.

An alternative process for the preparation of glycolic acid or its esters is disclosed in DE3133353C2. In this process, formaldehyde is reacted with carbon monoxide and water or an alcohol in an inert diluent in two reaction steps. In the first step, formaldehyde is reacted with carbon monoxide using an acidic, solid, insoluble, finely distributed catalyst at a ratio of hydrogen ion exchange capacity of the catalyst to the molar amount of the formaldehyde of 1:1 to 5:1, a temperature of 30° C. to 200° C. and a pressure of 10 to 325 bar. In the second step, water or an alcohol having 1 to 20 carbon atoms is added at a temperature of 20° C. to 200° C. and a pressure of 1 to 325 bar. The catalyst is subsequently mechanically separated from the reaction medium.

KR19950013078B1 relates to a process for producing glycolic acid in which formaldehyde and carbon monoxide are reacted in the presence of water or water-methanol mixture using a heterogeneous solid catalyst, which is polymeric strong acid catalyst ion-exchanged by 5-40 wt % with monovalent metal of Group 1B in a water-soluble inert solvent. Dioxane is used as a water-soluble inert solvent.

A similar process is described in KR19950013079B1 in which formaldehyde and carbon monoxide are reacted in the presence of water or water-methanol mixture using a polymeric strong acid catalyst in a water-soluble inert solvent.

A process for continuously manufacturing methyl glycolate from formaldehyde, carbon oxide and methanol is described in KR19950009480B1 in which a flow reactor filled with a polymeric strong acid catalyst is used. Reactant mixture of formaldehyde, water and inert solvent and carbon monoxide is supplied to the upper part of the reactor, and methanol is supplied to the lower part. In the upper part of the reactor, glycolic acid is produced via acid catalysis. In the lower part of the reactor, methyl glycolate is prepared from methanol and formed glycolic acid. The pressure of carbon monoxide is 500 to 6,000 psig and the temperature is 80 to 200° C. The suggested selectivity for this one-step procedure is relatively high.

KR0124821B1 relates to separating methylglycolate from an acidic solution. In this case, the reaction solution formed by a carbonylation reaction and an esterification reaction contains methyl glycolate, dioxane, water, methanol and hydrogen ion. This reaction solution is sent to a neutralization reactor and is neutralized by the addition of alkali to give a salt. The reaction solution containing salt is distilled to separate methanol, water and dioxane from methyl glycolate, salt and dioxane. The methanol separated from dioxane is recirculated to the carbonylation reactor. The solution which separated from the lower part of the distillation tower contains methyl glycolate, salt and dioxane. This is sent to a solid-liquid separator to separate the methyl glycolate from the solvent.

A further process for the production of methyl glycolate is described in KR19950011114B1. In this process formaldehyde is reacted with carbon monoxide to make a glycolic acid. The glycolic acid is then reacted with methanol to make a methyl glycolate. Residual formaldehyde is then reacted with methanol to make methylal. The methyl glycolate and methylal are then separated by distillation. The methylal is reacted with a Fe—Mo catalyst to return it to formaldehyde which is then recovered and concentrated before being recycled.

An alternative heterogeneous acid catalyst for the formaldehyde carbonylation reaction is described in U.S. Pat. No. 6,376,723. Sulfonic acid based ion exchange resins such as Amberlyst 38W and Nafion SAC13 are mentioned as suitable commercially available catalysts. Deloxan ASP 1/9, an alkyl sulfonic acid polysiloxane, is also listed as a suitable catalyst. This material is formed by co-polycondensation of propyl(3-sulfonic acid)siloxane and $SiO_2$.

He et al, in Catalysis Today, 51 (1999), 127-134, describe the use of heteropolyacids as homogeneous catalysts for the condensation of formaldehyde and methyl formate.

A still further process is described in JP2503178. In this process, glycolic acid is formed by hydrolysis of polyglycolide made from formaldehyde and carbon monoxide in the presence of a solid heteropoly acid.

WO2009/140787, WO2009/140788 and WO2009/140850 relate to processes using insoluble polyoxometalate compounds. These compounds either have specific acid properties or are encapsulated within zeolite cages, as solid acid catalysts, to produce glycolic acid from carbon monoxide and formaldehyde. However, the metal salts are prone to leaching of the metal component, which will reduce the number of active acid sites. In the case of zeolite impregnated with polyoxometalate salts, acid leaching will impact both the zeolite substrate and the salts themselves.

There are also a number of cases relating to various substituted organopolysiloxane compounds and their uses. These cases can be grouped into five families which cover different classes of polysiloxane compounds. The five groupings can be typified by: EP1360222B1, EP1786850B1, WO2006/013080A1, WO2007/090676A1 and US2010/0290962A1 which disclose various families of compounds. These documents suggest that these compounds may be useful for carbonylation reactions, but there is no detailed teaching as to how these materials can be used as catalysts for formaldehyde carbonylation in particular or to carbonylation reactions more generally.

It has been suggested that the use of heterogeneous catalysts will reduce the corrosion of the reaction system. None of the heterogeneous catalysts proposed in the prior art has been adopted commercially.

Although there have been numerous patents and publications relating to the production of ethylene glycol from glycolic acid which is formed by carbonylation of formaldehyde, there remains a need for an improved process which can compete economically with the established industrial production route.

The various approaches to trying to solve the problems associated with the reaction can be summarised into two categories. The first relates to the investigation of homogeneous catalyst systems which operate at lower pressure and lower acid concentration than has previously been achievable.

The second relates to the investigation of heterogeneous solid acid catalysts as these benefit from easier separation of the catalyst and reduced reactor corrosion. However, the solid catalysts proposed to date have also proved to have a number of shortcomings and have not been adopted commercially. These catalysts generally lack the thermal and chemical stability required to withstand the severe reaction conditions.

For example, aluminosilicate zeolites are not stable under highly acidic conditions, as the aluminium is leached from the structure causing it to collapse. This results in loss of activity and eventually complete disintegration of the catalyst (Pan et al, 1994, Studies in Surface Science and Catalysis). With a view to avoid this problem, it is proposed in EP0114657 that the reaction should be operated such that the amount of acid formed is limited, but this reduces the efficiency of the reactor and exacerbates separation problems.

It is well known that sulfonic acid based ion exchange resins have limited thermal stability in aqueous environments leading to a loss of acid groups. Furthermore it has been found that formaldehyde attacks the aromatic rings within styrene/di vinyl benzene based resins causing swelling and further loss of acid groups.

It has been shown that substituted organopolysiloxane compounds, such as Deloxan ASP 1/9, Quadrasil-SA and Silicycle (SCX-2), and alkyl sulfonic acid polysiloxanes, can be used but these have been found to quickly lose catalytic performance at effective process conditions. This has been attributed to the loss of the tethered organic acid groups due to hydrolysis.

There therefore remains a need to provide a process for the production of ethylene glycol via the carbonylation of formaldehyde to glycolic acid economically viable. The process will also be suitable for other carbonylation reactions and will address corresponding problems associated with these reactions.

In investigating the problem of solid acid catalyst stability in the formaldehyde carbonylation environment a large number of materials have been tested. In the course of this testing, it was observed that the initial activity of a functionalized catalytic silica material reduced with time. By 'functionalized', we mean that the silica material has acid groups, for example, alkyl sulphonic acid groups, tethered to the silica support. It has been discovered that the reduction in activity is a function of removal of the tethered functionalized groups.

However, it was surprisingly discovered that when the reaction is carried out in the presence of a small quantity of an homogeneous alkyl silyl sulfonic acid, that the reduction in activity of the silica material can be recovered or avoided. In some situations an enhanced activity can be achieved.

Thus according to a first aspect of the present invention there is provided a process for the production of glycolic acid or derivatives thereof from formaldehyde comprising reacting formaldehyde with carbon monoxide and water in the presence of a silica catalyst, wherein from about 200 to about 5000 ppm of an alkyl silyl sulfonic acid is supplied to the reaction.

Without wishing to be bound by any theory, it is postulated that the presence of the alkyl silyl sulfonic acid enables the silica catalyst to become at least functionalized.

Any suitable amounts of alkyl silyl sulfonic acid may be used. In one arrangement from about 300 to about 3000 ppm, from about 500 to about 1500 ppm, or from 750 to about 1000 ppm. It will be understood that ppm of the sulphur present.

Any suitable silica catalyst may be used. It may be non-porous or porous. In one arrangement where the catalyst is porous, it may have a surface area of from about 250 to about 500 m$^2$ and a pore volume of from about 0.2 to 1 cc/g. As supplied to the reactor it may be functionalised or unfunctionalised.

Examples of suitable silicas include those from the Johnson Matthey QuadraSil range including SA, TA, AP or MP or QuadraSil PHI available from Sigma Aldrich.

In one arrangement, the solid component may be unfunctionalised. By "unfunctionalised" we mean that the surface has not been specifically modified to add active catalytic moieties to the surface.

In a second arrangement, the solid component may be a functionalised material. By 'functionalised' we mean that the material has been modified to have enhanced activity. In one arrangement, the functionalization may be to add alkyl silyl sulfonic acid groups, hydroxyl groups or both alkyl silyl sulfonic acid groups and hydroxyl groups on the surface of the material.

Any suitable alkyl silyl sulfonic acid may be used. Suitable acids include trihydroxysilylalkyl sulfonic acid, such as trihydroxysilylpropyl sulfonic acid, or trihydroxysilylethyl sulfonic acid.

The alkyl silyl sulfonic acid may be fresh alkyl silyl sulfonic acid or its addition may be achieved by recycling a portion of the product stream recovered from the reactor which will include alkyl silyl sulfonic acid.

The alkyl silyl sulfonic acid will be added in an amount of from about 200 ppm to about 5000 ppm. Amounts in a region of about 300 ppm to about 1000 ppm or about 500 ppm may offer some advantages.

The use of recycled acid may offer advantages since it has been seen that when recycled acid was passed over aged functionalised silica, the catalytic effect of these recycled species were surprisingly greater than would be expected from the acid concentration in the liquid phase.

Derivatives of glycolic acid include glycolic acid dimers, esters of glycolic acid, and if an alcohol is present, ester related adducts.

The water may be present in any suitable amount. It may be used in an amount from the stoichiometric requirement to a molar ratio of about 4:1 water:formaldehyde.

The water may additionally act as the solvent for the reaction. Where water is used as a solvent it will be used in an amount in excess of the ratio detailed above. The water may be provided separately. Alternatively or additionally it may be supplied in the aldehyde feed or with another solvent.

Alternatively the water may be present in an amount which is sufficient for the reaction and a separate solvent may be used.

Where a solvent is to be used, it may be the reaction product itself or a separate solvent. Suitable separate solvents include carboxylic acids or sulphones. Suitable solvents include propionic acid or a sulphone. 2,3,4,5-tetrahydrothiophene-1,1-dioxide may be a suitable sulphone.

The formaldehyde may be supplied as a solution in water or generated in situ within the reactor. For example, in one embodiment of the invention, paraformaldehyde is used as a reactant. Paraformaldehyde is a polymer of formaldehyde, which reverts to monomeric formaldehyde in the presence of polar molecules, such as water or alcohol solvents.

The carbon monoxide can be a pure source of carbon monoxide, optionally comprising small quantities of impurities such as one or more of light alkanes, carbon dioxide or hydrogen. Alternatively, the carbon monoxide source can be a component of a gaseous mixture, for example synthesis gas (syngas) which is a mixture of hydrogen and carbon monoxide.

The temperature of the reaction is typically in the range of from about 50° C. to about 400° C., for example in the range of from about 100° C. to about 250° C. and the pressure at which reaction is carried out is typically in the range of from about 1 to about 1000 bara (about 0.1 to about 100 MPa), such as in the range of from about 10 to about 200 bare (about 0.1 to about 20 MPa).

The process can be carried out in any suitable manner. In one arrangement it may be conducted in a continuous flow configuration in which carbon monoxide, water, formaldehyde, and optional solvent, either pre-mixed or separately, are introduced to a fixed bed or slurry reactor containing the silica catalyst to produce a product composition which is continuously withdrawn from the reactor. The reaction can take place in single or multiple reactors which may be of different types arranged in either series or parallel configuration. One or more of the feedstocks may be added at a single point or sequentially as the reaction progresses.

In one alternative arrangement, the reaction can be conducted batch-wise. In one embodiment this involves suspending and stirring a suspension of the silica catalyst in a liquid reaction composition comprising solvent and aldehyde, with carbon monoxide being fed into the reactor under pressure. The resulting product composition can then be periodically removed from the reactor.

Howsoever formed, the product stream recovered from the reactor comprises the desired acid. The product stream can be treated to recover one or more of the solvent, unreacted reactants and the homogeneous catalytic component, for example formaldehyde and carbon monoxide. This can be achieved by a variety of means. For example, formaldehyde and carbon monoxide can be recovered by flash separation and/or distillation. The product stream may include derivatives of glycolic acid.

Figure 2:
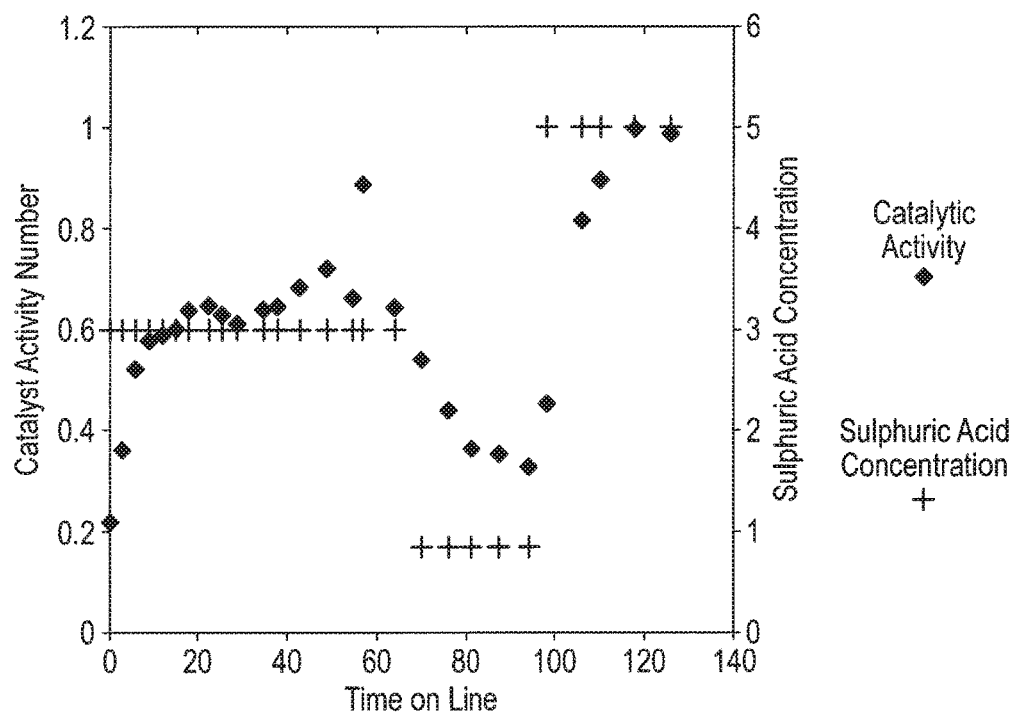

The present invention will now be described by way of example with reference to the following examples and figures in which:

FIG. 1 is a graph illustrating the effect of concentration on activity from Example 1; and FIG. 2 is a graph illustrating the effect of sulphur in Example 1.

EXAMPLE 1

In this example, the use of a liquid acid catalyst and a silica support for the hydrocarbonylation of formaldehyde to glycolic acid. The acid catalysts used at various times during the life of the catalyst were sulphuric acid, ethane sulfonic acid and trihydroxylsilylpropane sulfonic acid in varying quantities. The reaction was carried out at a temperature of 160° C. and a pressure of 170 bar(g). The feed flow of formaldehyde was 150 mL/h and the gas flow of carbon dioxide was 50 L/h. A graph illustrating how activity is affected by changing homogeneous acid concentration is illustrated in FIG. 2.

It can be seen that the homogeneous acid trihydroxylacids interact closely with the silica support. From FIG. 2 it can be seen that the glycolic acid make increases after the feed acid is increased at 100 hours but this takes 20 hours to reach a steady activity. The effect of turning off the homogeneous silyl sulfonic acid in the feed is illustrated in FIG. 2 between 60 and 95 hours and again there is an extended time lag between the removal of acid from the feed and the reduction of the activity to a steady state.

FIG. 1 illustrates the 'chromatographic' effect is that the liquid feed/product have a residence time of under 1 hour (48 minutes) whereas the sulphur release over 24 hours later in the test run.

EXAMPLE 2

The liquid feed for this example comprised 10% formaldehyde, 12% water and 78% glycolic acid. The feed then had sulfuric acid added to make up the desired sulfuric acid concentration.

A fixed bed reactor was loaded with 120 ml of 3 mm smooth glass balls. The reactor was then pressurised to 170 bar(g) with carbon monoxide and heated to 160° C. Once at reaction conditions the carbon monoxide flow to the reactor was set at 50 NL/h and the liquid feed containing 0% sulfuric acid was started at 150 mL/h. The reactor was set to pressure control at 170 bar(g) with any excess carbon monoxide being vented and the liquid product recovered. After 42 hours the feed was switched to 3 wt % sulfuric acid liquid feed. After 80 hours the feed was switched to 5 wt % sulphuric acid liquid feed. The results are set out in Table 1.

This example shows that feeding a homogeneous acid over an inert, non-porous, material does not give the same enhanced activity observed when the homogeneous catalytic moiety reacts with the support as in Example 1.

EXAMPLE 3

The liquid feed for the example was 10 wt % formaldehyde, 12 wt % water and 78 wt % glycolic acid. This feed then had silyl sulfonic acid added to make up to the desired sulfonic acid concentration.

A fixed bed reactor was loaded with 205 mL of unfunctionalized silica chips with a surface area of 415 m2/g and a pore volume of 1.02 ml/g. The reactor was then pressurised to 170 bar(g) with carbon monoxide and heated to 160° C. Once at reaction conditions the carbon monoxide flow to the reactor was set at 50 NL/h and the liquid feed containing 0% acid was started at 150 ml/h. The reactor was set to pressure control at 170 bar(g) with any excess carbon monoxide being vented and the liquid product recovered. After 175 hours 500 ppm tri-hydroxysilyl propane sulfonic acid (silyl sulfonic acid) feed was started. After 248 hours the feed was switched to 1000 ppm silyl sulfonic acid liquid feed. After 282 hours the feed was switched to 500 ppm silyl sulfonic acid and 3 wt % sulfuric acid liquid feed. After 300 hours the feed was switched to 1 wt % silyl sulfonic acid liquid feed. The results are set out in Table 1 and show that the porous silica does not need to be functionalized prior to reaction to exhibit improved performance.

EXAMPLE 4

The liquid feed for this example was 10 wt % formaldehyde, 12 wt % water and 78 wt % glycolic acid. The recycled product feed was the product from the start of the run containing 387 ppm silyl sulfonic acid groups which had been washed from the functionalised support. This product was dosed to contain 10 wt % formaldehyde so it could be passed back through the reactor.

A fixed bed reactor was loaded with 120 ml of functionalised silica chips. The silica was functionalised with silyl sulfonic acid groups. The reactor was then pressurised to 170 bar(g) with carbon monoxide and heated to 160° C. Once at reaction conditions the carbon monoxide flow to the reactor was set at 50 NL/h and the liquid feed was started at 150 ml/h. The reactor was set to pressure control at 170 bar(g) with any excess carbon monoxide being vented and the liquid product recovered. At the start of the run a large proportion of the functional silyl sulfonic acid groups were washed from the support. This product was recovered for dosing with formaldehyde to be passed back through the reactor. A large boost in formaldehyde conversion was observed when this silyl sulfonic acid containing feed was brought online in comparison to feed which contained no sulfonic acid species. The results are set out in Table 1.

The result shows that the active component can be recycled back to the reactor and activity can be recovered.

TABLE 1

| Example | Solid Component | Homogeneous Component | Inlet Temp ° C. | Pressure Bar (g) | Formaldehyde Conversion % | Reactor Residence Time h |
|---|---|---|---|---|---|---|
| 4 | Glass Balls | None | 160 | 170 | 0 | 0.27 |
| | | 3% wt sulphuric acid | 160 | 170 | 5.4 | 0.27 |
| | | 5% wt sulphuric acid | 160 | 170 | 12.6 | 0.27 |
| 5 | Unfunctionalized Silica Chips | None | 160 | 170 | 0 | 0.52 |
| | | 500 ppm (w) Silyl Sulphonic Acid | 160 | 170 | 39.6 | 0.52 |
| | | 1000 ppm (w) Silyl Sulphonic Acid | 160 | 170 | 40.5 | 0.52 |
| | | 1 wt % Silyl Sulphonic Acid | 160 | 170 | 45 | 0.52 |

TABLE 1-continued

| Example | Solid Component | Homogeneous Component | Inlet Temp °C. | Pressure Bar (g) | Formaldehyde Conversion % | Reactor Residence Time h |
|---|---|---|---|---|---|---|
| | | 500 ppm (w) Silyl Sulphonic Acid + 3% wt sulphuric acid | 160 | 170 | 72.5 | 0.52 |
| 6 | Functionalised Silica Chips | None | 160 | 176 | 21.6 | 0.46 |
| | | Recycled Product (387 ppm (w)) Silyl Sulphonic Acid | 160 | 176 | 39.9 | 0.46 |

The invention claimed is:

1. A process for the production of glycolic acid or derivatives thereof from formaldehyde comprising reacting formaldehyde with carbon monoxide and water in the presence of a silica catalyst, wherein from about 200 to about 5000 ppm of an alkyl silyl sulfonic acid is supplied to the reaction.

2. The process according to claim 1, wherein the silica is porous.

3. The process according to claim 1, wherein the silica has a surface area of from about 250 to about 500 m2 and a pore volume of from about 0.2 to 1 cc/g.

4. The process according to claim 1, wherein the silica is functionalised.

5. The process according to claim 4, wherein the functionalization is the presence of acid groups tethered to the silica support.

6. The process according to claim 5, wherein the acid groups are alkyl sulfonic acid groups.

7. The process according to claim 1, wherein the alkyl silyl sulfonic acid is trihydroxysilylalkyl sulfonic acid, such as trihydroxysilylpropyl sulfonic acid, or trihydroxysilylethyl sulfonic acid.

8. The process according to claim 1, wherein the alkyl silyl sulfonic acid is supplied in a recycle product stream.

9. The process according to claim 1, wherein the alkyl silyl sulfonic acid is added in an amount of from about 300 ppm to about 500 ppm.

10. The process according to claim 1, wherein the water is present in an amount from the stoichiometric requirement to a molar ratio of about 4:1 water:formaldehyde.

11. The process according to claim 1, wherein the reaction is carried out in the presence of a solvent.

12. The process according to claim 11, wherein the solvent is water, a carboxylic acid, or a sulphone.

13. The process according to claim 1, wherein the process is carried out at a temperature of from about 50° C. to about 400° C.

14. The process according to claim 1, wherein the process is carried out at a pressure of from about 1 to about 1000 bara.

15. The process according to claim 12, wherein the carboxylic acid is propionic acid and the sulphone is 2,3,4, 5-tetrahydrothiophene-1, 1-dioxide.

16. The process according to claim 13 where the process is carried out at a temperature of from about 100° C. to about 250° C.

17. The process according to claim 14 where the process is carried out at a pressure of from about 10 to about 200 bara.

* * * * *